United States Patent [19]
Infinger et al.

[11] Patent Number: 5,464,432
[45] Date of Patent: Nov. 7, 1995

[54] IMPLANTABLE ATRIAL DEFIBRILLATOR HAVING AN INTERMITTENTLY ACTIVATED FIBRILLATION DETECTOR

[75] Inventors: Kenneth R. Infinger, Redmond; Joseph M. Bocek, Seattle, both of Wash.

[73] Assignee: InControl, Inc., Redmond, Wash.

[21] Appl. No.: 232,767

[22] Filed: Apr. 25, 1994

[51] Int. Cl.⁶ .................................................... A61N 1/39
[52] U.S. Cl. .................................... 607/5; 607/4; 607/14
[58] Field of Search ................................. 607/4, 5, 9, 14

[56] References Cited

U.S. PATENT DOCUMENTS 5,282,836  2/1994  Kreyenhagen et al. .................... 607/4
5,282,837  2/1994  Adams et al. ............................... 607/4
5,366,486  11/1994  Zipes et al. ............................. 128/705

*Primary Examiner*—William E. Kamm
*Assistant Examiner*—Marianne Parker
*Attorney, Agent, or Firm*—Richard O. Gray, Jr.

[57] ABSTRACT

An implantable automatic atrial defibrillator powered by a depletable battery power source conserves battery power for extending the predicted life of the defibrillator by intermittently detecting for atrial fibrillation. The atrial defibrillator includes a real time clock which, at spaced apart predetermined times, causes heart activity data to be stored in a memory. Thereafter, a normally deactivated atrial fibrillation detector is activated for processing the stored data to detect for atrial fibrillation.

5 Claims, 1 Drawing Sheet

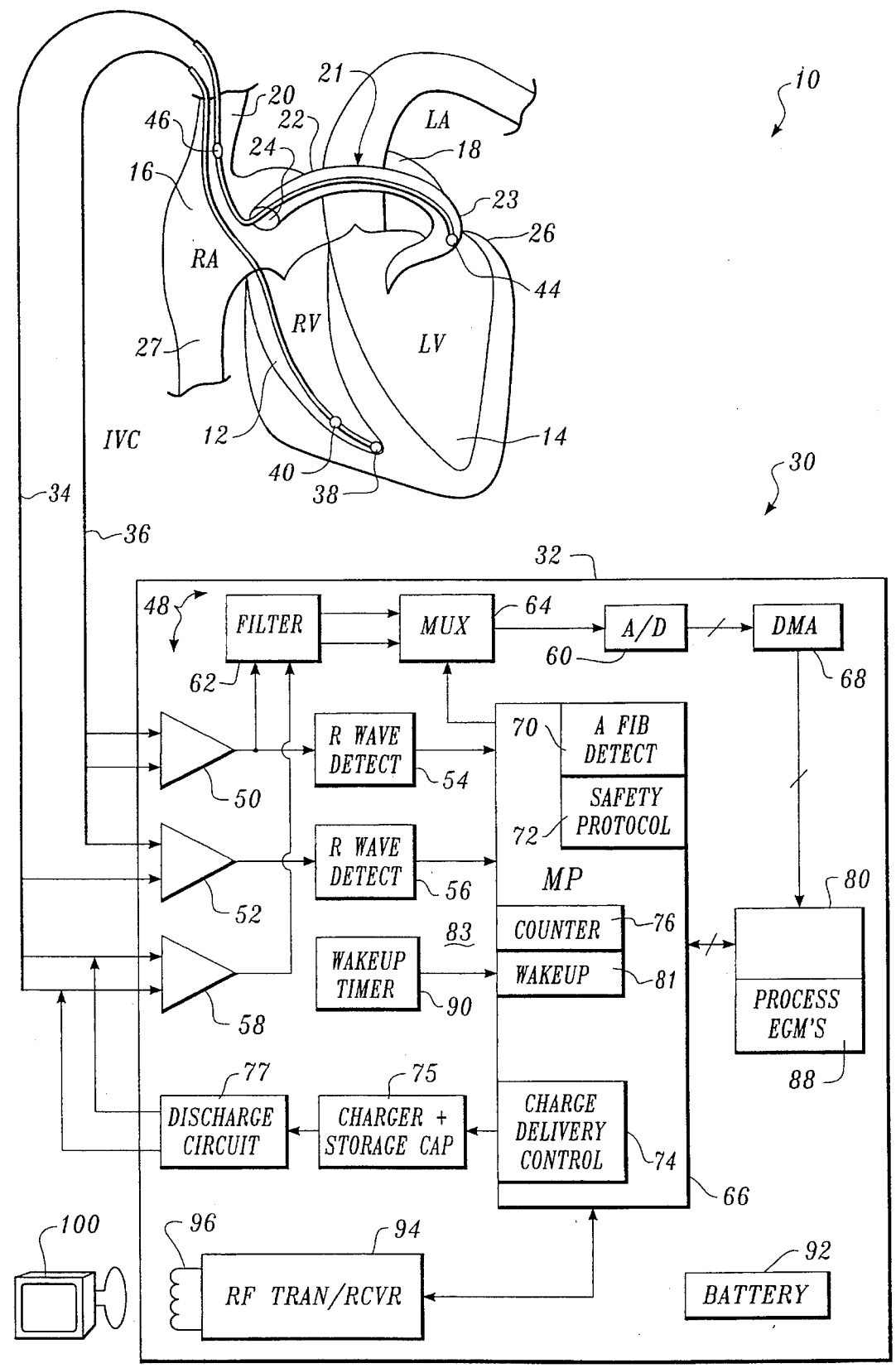

IMPLANTABLE ATRIAL DEFIBRILLATOR HAVING AN INTERMITTENTLY ACTIVATED FIBRILLATION DETECTOR

BACKGROUND OF THE INVENTION

The present invention generally relates to an automatic implantable atrial defibrillator for delivering cardioverting or defibrillating electrical energy to the atria of a human heart. The present invention is more particularly directed to such an atrial defibrillator which has an intermittently activated atrial fibrillation detector which provides reduced power consumption of a depletable power source, such as a battery, within the atrial defibrillator.

Atrial fibrillation is probably the most common cardiac arrhythmia. Although it is not usually a life threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality.

Implantable atrial defibrillators proposed in the past have exhibited a number of disadvantages which probably has been the cause of these defibrillators from becoming a commercial reality. Two such defibrillators, although represented as being implantable, were not fully automatic, requiring human interaction for cardioverting or defibrillating the heart. Both of these defibrillators require the patient to recognize the symptoms of atrial fibrillation with one defibrillator requiring a visit to a physician to activate the defibrillator and the other defibrillator requiring the patient to activate the defibrillator from external to the patient's skin with a magnet.

Implantable ventricular defibrillators for applying defibrillating electrical energy to the ventricles of the heart are well known and have been commercially available for a number of years. Because ventricular fibrillation is life threatening, resulting in unconsciousness in just a few seconds and leading to death in just a few minutes, implantable ventricular defibrillators are fully automatic for detecting ventricular fibrillation and quickly applying the defibrillating electrical energy to the ventricles. Such defibrillators are quite large in physical size as compared to the size of a pacemaker, for example, because of the rather large battery and storage capacitors required for providing defibrillating energies of ten joules of more. Due to their rather large size, these devices must be implanted in an abdominal region of the human body.

Any form of implantable device must be powered by a portable, depletable power source, such as a battery. When the battery is depleted of its energy, it is necessary to explant the device and implant a replacement. As a result, for an implantable device to be considered commercially viable, it is generally believed that the device should have a predicted lifetime of a number of years, such as five years, for example.

Predicted lifetimes of less than five years for ventricular defibrillators have not diminished the commercial nature of these devices because ventricular fibrillation is life threatening. However, since atrial fibrillation is not generally considered to be life threatening, it is generally believed that atrial defibrillators should have lifetimes on the order of five years to render such devices commercial in nature. To further enhance the commercial nature of these devices, it is desirable to limit the physical size of an atrial defibrillator to the size of a large pacemaker, for example, to permit the atrial defibrillator to be implanted, like a pacemaker, within the chest of the human body. While predicted lifetime and physical size have not adversely affected the commercial nature of ventricular defibrillators, such constraints have probably been the cause of an atrial defibrillator not being commercially available to date.

It has long been believed that as much electrical energy is required to cardiovert or defibrillate the atria of the heart as is required to cardiovert or defibrillate the ventricles of the heart, on the order of ten joules or more. Furthermore, episodes of atrial fibrillation occur much more frequently than do episodes of ventricular fibrillation. As a result, due to the contemplated required cardioverting or defibrillating energy levels for cardioverting or defibrillating the atria of the heart and the predicted required frequency of delivering such energies, it has long been believed that an implantable atrial defibrillator would either have an unreasonably short and commercially unacceptable predicted lifetime or a battery and storage capacitor of such a large size that the atrial defibrillator would be too large in physical size. Fortunately, a lead system has been discovered for an atrial defibrillator which greatly reduces the amount of energy required to defibrillate or cardiovert the atria. This lead system is fully described in U.S. Pat. No. 5,279,291 which issued on Jan. 18, 1994 for "Method for Atrial Defibrillation", which is assigned to the assignee of the present invention, and which is incorporated herein by reference. The lead system described in that patent includes a first electrode in the coronary sinus or great cardiac vein of the heart and a second electrode in the right atrium or superior vena cava of the heart. With such electrode placement, cardioverting energy applied to these electrodes is substantially confined to the atria, reducing the amount of energy required to cardiovert the atria to on the order of one joule or less.

It has also long been believed that an atrial defibrillator, like a ventricular defibrillator, should charge its storage capacitor quickly to permit essentially immediate cardioversion. Such quick storage capacitor charging places an extreme drain on the battery thereby further limiting the predicted lifetime of an implantable atrial defibrillator and further adding to the heretofore perceived non-commercial nature of these devices.

Recently, it has been recognized that, since atrial fibrillation is not life threatening, the storage capacitor of an atrial defibrillator need not be charged as quickly as the storage capacitor of a ventricular defibrillator. That recognition has led to another improvement in an atrial defibrillator fully described in U.S. Pat. No. 5,251,624 for "Pulse Generator for Use in an Implantable Atrial Defibrillator" which issued on Oct. 12, 1993, which is assigned to the assignee of the present invention and which is also incorporated herein by reference. The pulse generator described in that patent conserves battery power while still providing adequate electrical energy to cardiovert or defibrillate the atria of the heart to arrest atrial fibrillation. This is achieved by charging the storage capacitor comparatively slowly to minimize drain on the defibrillator battery but in sufficient time to arrest the atrial fibrillation. In accordance with the described preferred embodiment, this is accomplished by converting the rather low voltage of the battery to a pulsating high voltage of 300 to 400 volts, for example, with a flyback transformer having a primary winding coupled to an oscillator which provides the primary winding with a high frequency, low duty cycle input. By virtue of this arrangement, sufficient electrical energy for cardioverting or defibrillating the heart is stored in the storage capacitor without imposing a high drain on the defibrillator battery. Even though a minute may be required to fully charge the storage capacity, this is sufficient to arrest the atrial fibrillation and bring comfort to the patient.

Lastly, since ventricular fibrillation is life threatening, ventricular defibrillators continuously sense activity of the heart and detect for fibrillation. While sense amplifiers used to sense heart activity are generally perceived as consuming little power, the power consumed by these circuits through continuous operation over periods of months and years is considerable. Further, the continuous analysis of the sensed heart activity over time amounts to still further considerable power being consumed. Hence, the power consumed during the continuous sensing of heart activity and detection for fibrillation by an implantable device cannot be ignored when predicting the lifetime of the device. Until the present invention, it was also generally believed that a fully automatic atrial defibrillator should continuously sense heart activity and detect for fibrillation. Hence, this further power consumption factor has also contributed to the perceived non-commercial nature of an implantable, fully automatic, atrial defibrillator due to unacceptable predicted lifetimes.

SUMMARY OF THE INVENTION

An implantable atrial defibrillator applies cardioverting electrical energy to the atria of a human heart in need of cardioversion. The atrial defibrillator includes lead means for sensing electrical activity of the heart including the atria of the heart and atrial fibrillation detecting means for detecting atrial fibrillation of the heart. The atrial fibrillation detecting means is in a normally deactivated state. The atrial defibrillator further includes cardioverting means coupled to the lead means and is responsive to the atrial fibrillation detecting means detecting atrial fibrillation of the heart for applying cardioverting electrical energy to the atria of the heart to cardiovert the atria of the heart and activating means for activating the atrial fibrillation detecting means at spaced apart predetermined times.

The atrial defibrillator may further include data acquiring means coupled to the lead means for acquiring data associated with the sensed activity of the heart. The data acquiring means includes memory means for storing the acquired data. The atrial fibrillation detecting means may further include processing means for processing the stored data for detecting atrial fibrillation of the heart, wherein the data acquiring means is normally in a deactivated state. The activating means activates the data acquiring means prior to activating the atrial fibrillation detecting means.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the sole FIGURE of which like reference numerals identify identical elements, and wherein the sole FIGURE is a schematic block diagram of a fully implantable atrial defibrillator embodying the present invention.

DETAILED DESCRIPTION OF THE PREFERRED EMBODIMENT

Referring now to FIG. 1, it illustrates an implantable automatic atrial defibrillator 30 embodying the present invention.

The atrial defibrillator 30 includes an implantable enclosure 32 and an implantable lead system including an intravascular lead 34 and an endocardial lead 36. The endocardial lead 36 has tip and ring electrodes 38 and 40 respectively adapted for placement in the right ventricle 12. The intravascular lead 34 has a tip electrode 44 adapted for placement in the coronary sinus 22 or the great cardiac vein 23 and a ring electrode 46 adapted for placement in the superior vena cava 20 or right atrium 16. An alternative lead system may include separate leads for electrodes 44 and 46. This requires an additional endocardial lead (not shown in FIG. 1) adapted for placing electrode 46 in the superior vena cava 20 or the right atrium 16.

Electrodes 44 and 46 of lead 34 sense atrial activity of the heart. Electrodes 44 and 46 perform the additional function of applying cardioverting electrical energy across the atria 16 and 18 of the heart.

Electrodes 38 and 40 sense R waves of the heart and may be referred to herein as the first electrode pair. Electrode 44 together with either electrode 38 or electrode 40 also sense R waves of the heart and may be referred to herein as the second electrode pair. The dual sensing of the R waves between the first and second electrode pairs is performed for the purpose of reliably sensing the R waves as fully described in copending U.S. patent application Ser. No. 07/861,184, filed on Mar. 31, 1992 for "Apparatus and Method for Reliably Detecting a Depolarization Activation Wave of the Heart and Atrial Defibrillator Utilizing Same" and which is assigned to the assigned of the present invention.

The implantable enclosure 32 includes a microprocessor 66 and a memory 80. The microprocessor controls the overall function of the atrial defibrillator 30 under software controlled by operating instructions stored in a memory 80. The memory 80 includes a process memory portion 88 for storing electrocardiogram data samples to be processed by the microprocessor 66 as will be described subsequently.

Within the enclosure 32, the atrial defibrillator 30 further includes a data acquisition means 48 including sense amplifiers 50, 52, and 58, filter 62, multiplexer 64, analog-to-digital converter 60, direct memory access controller 68, and memory 80. Sense amplifier 50 is coupled to electrodes 38 and 40 of lead 36 and sense amplifier 52 is coupled to electrode 44 of lead 34 and to either electrode 38 or electrode 40 of lead 36. The sense amplifiers 50 and 52 amplify the electrocardiogram signals provided by the first and second pairs of electrodes respectively and provide R wave detectors 54 and 56 respectively with an amplified output. The R wave detectors 54 and 56 each include a threshold circuit which isolates the R waves from the amplified electrocardiograms provided by sense amplifiers 50 and 52. The outputs of the R wave detectors 54 and 56 are coupled to the microprocessor for conveying the isolated R waves to the microprocessor 66.

Sense amplifier 58 is coupled to electrodes 44 and 46 of lead 34. The sense amplifier 58 provides an amplified output of the electrocardiograms sensed by the first electrode pair consisting of electrodes 44 and 46. The electrocardiograms provided by sense amplifier 58 predominantly represent atrial activity of the heart 10.

The outputs of the sense amplifiers 50 and 58 are coupled to an analog-to-digital converter 60 through the filter 62 and the multiplexer 64. The analog-to-digital converter 60 digitizes the electrocardiograms provided by the amplifiers 50 and 58 to generate electrocardiogram digital data samples. The electrocardiogram samples are conveyed to the direct memory access 68 which then stores the electrocardiogram samples in memory portion 88 of memory 80.

In controlling the function of the atrial defibrillator 30, the microprocessor 66 implements an atrial fibrillation detection algorithm represented by an atrial fibrillation detector 70. When the atrial fibrillation detector 70 determines that the heart 10 is in atrial fibrillation, the microprocessor 66 under software control performs charge and delivery control operations pursuant to operating instructions obtained from the memory 80 to implement the charge and delivery control 74. The charge and delivery control 74 first causes the charger of circuit 75 to charge the storage capacitor therein to a selected peak voltage. The charge and delivery control 74 monitors the charging of the capacitor. When the charge delivery control 74 determines that the voltage across the storage capacitor has reached a selected peak voltage, the microprocessor through the charge and delivery control 74 terminates the charging.

After the charging of the storage capacitor is completed, the microprocessor implements a safety protocol 72. This confirms that R waves are being reliably sensed and detects for a cardiac interval which is longer than a preselected minimum time interval as fully described in U.S. Pat. No. 5,207,219 which issued on May 4, 1993 for "Atrial Defibrillator and Method for Providing Interval Timing Prior to Cardioversion" and which is assigned to the assignee of the present invention.

Upon the successful completion of the safety protocol, the charge and delivery control 74 causes a discharge circuit 77, which is coupled to the storage capacitor of circuit 75, to discharge a portion of the energy stored in the storage capacitor. The discharged energy is applied to electrodes 44 and 46 of the intravascular lead 34 for applying the cardioverting electrical energy to the atria 16 and 18 of the heart 10.

After the cardioverting energy is applied to the atria, the atrial defibrillator 30 determines if the cardioversion was successful in arresting the atrial fibrillation episode. If the cardioversion was not successful, the atrial fibrillation detector 70 once again detects for the presence of atrial fibrillation. Then, the cardioversion sequence is repeated at a next higher energy level.

Lastly, the atrial defibrillator 30 includes an RF transmitter/receiver 94 within enclosure 32. The RF transmitter/receiver includes a coiled antenna 96 for communicating through telemetry to an external programmer 100. The telemetry link provided by the RF transmitter/receiver 94 and the external programmer 100 permits the cardiologist to program the atrial defibrillator 30 with respect to its various programmable parameters and to enable the cardiologist to read from the atrial defibrillator 30 certain data which has been stored in the memory 80.

The entire cardioversion sequence from original detection of an atrial fibrillation episode through successful cardioversion is initiated at spaced apart predetermined times under the control of an activating means 83 including a wakeup timer 90 and a wakeup 81 of microprocessor 66. The predetermined times are a programmable parameter of the atrial defibrillator 30 and provides wakeup of the atrial defibrillator 30 at spaced apart times for the detection and cardioversion of atrial fibrillation. As a result, the wakeup timer 90 may be reset after the completion of each therapy and after the completion of each atrial fibrillation detection which does not require intervention.

Atrial fibrillation is not a life-threatening malady. Hence, unlike ventricular defibrillators which must continuously detect for ventricular fibrillation, the atrial defibrillator 30 detects for atrial fibrillation at spaced apart times which are predetermined by the time interval to be timed by the wakeup timer 90. Atrial fibrillation detection may be initiated once every minute to once every twenty minutes for example in order to conserve power provided by a battery 92 which powers the atrial defibrillator while still assuring timely intervention for the patient.

The manner in which the atrial defibrillator 30 detects an atrial fibrillation episode and cardioverts the atrial fibrillation episode will now be described. The microprocessor 66 and hence the atrial fibrillation detector 70 are normally in a deactivated state along with sense amplifiers 50, 52, and 58, R wave detectors 54 and 56, multiplexer 64, analog-to-digital converter 60, direct memory access 68, and memory 80. As previously mentioned, when the wakeup timer 90 times a predetermined time interval, it causes the wakeup 81 of the atrial defibrillator 30 to initiate detection of a possible atrial fibrillation episode. When the atrial defibrillator 30 is to detect for an atrial fibrillation episode, the wakeup timer 90 first activates the wakeup 81 of the microprocessor 66 which then activates the sense amplifiers 50, 52, and 58, the analog-to-digital converter 60, the direct memory access 68, and the memory 80, to initiate an eight second acquisition period. During this acquisition period, the microprocessor 66 causes the multiplexer 64 to alternately couple the outputs of sense amplifiers 50 and 58 to the analog-to-digital converter 60 to permit the storing of digital samples of the electrocardiograms sensed by electrodes 44 and 46 of lead 34 and electrodes 38 and 40 of lead 36. The electrocardiogram digital samples for the entire eight seconds are stored in the process memory portion 88 of the memory 80.

When the eight second acquisition is completed, the microprocessor 66 implements the atrial fibrillation detector 70 by processing the data stored in the process memory portion 88 to detect for atrial fibrillation in accordance with an atrial fibrillation detection algorithm. If atrial fibrillation is not detected, the wakeup 81 of the microprocessor deactivates the data acquisition means 48, resets the wakeup timer 90, and then deactivates the microprocessor 66. The wakeup timer 90 then proceeds to time its predetermined time interval to once again activate the wakeup 81 of microprocessor 66 at the next time in which a possible atrial fibrillation episode is to be detected.

If atrial fibrillation is detected by the atrial fibrillation detector 70, the charge delivery control 74 causes the charge and storage capacitor circuit 75 to charge the storage capacitor to a preselected peak voltage. When the capacitor is charged, the atrial fibrillation detector 70 determines if the atria 16 and 18 of the heart 10 are still in fibrillation. In doing so, the atrial defibrillator will perform another eight second acquisition period. The electrocardiogram samples acquired during this further eight second acquisition period are used to overwrite the previously-stored electrocardiogram samples in the process memory portion 88.

If the atrial fibrillation detector 70 determines that the atria are not still in fibrillation, the process is completed and the wakeup 81 deactivates the data acquisition means 48, resets the wakeup timer 90, and then deactivates the microprocessor 66. The wakeup timer 90 then proceeds to time its predetermined time interval. However, if the atria are still in fibrillation, the microprocessor 66 then implements the safety protocol 72. The safety protocol detects for a cardiac interval which is longer than a preselected minimum interval. More specifically, the R wave detectors 54 and 56 isolate the R wave of each cardiac cycle. When the safety protocol 72 of the microprocessor 66 detects two immediately successive R waves which are spaced apart in time by a time greater than the preselected minimum interval, the safety protocol is completed.

When the safety protocol is completed, the charge delivery control 74 causes the discharge circuit 77 to discharge a portion of the energy stored in the storage capacitor of circuit 75 between electrodes 44 and 46 for cardioverting the atria of the heart.

Following the delivery of the cardioverting electrical energy to the atria, the atrial fibrillation detector 70 will once again determine if atrial fibrillation is still present. In doing so, a further eight second data acquisition is performed. If the atria have been successfully cardioverted, the process is completed and the wakeup 81 deactivates the data acquisition means 48, resets the wakeup timer 90, and then deactivates the microprocessor 66. The wakeup timer 90 then proceeds to time its predetermined time interval and will once again initiate the detection of a possible atrial fibrillation episode at the next predetermined time.

If it is determined that the heart is still in atrial fibrillation, the microprocessor through a counter 76 determines if the atria, for this fibrillation episode, have been provided with cardioverting electrical energy a predetermined number of times. If the atria have been provided with cardioverting electrical energy a predetermined number of times without successfully cardioverting the atria, the process is considered completed and the wakeup 81 deactivates the data acquisition means 48, resets wakeup timer 90, and then deactivates the microprocessor 66. If, however, additional cardioversion attempts remain, the atrial defibrillator 30 will recharge the capacitor of circuit 75 in the same manner as previously described and the cardioversion sequence is repeated, but at a higher energy level.

As a result of the foregoing, the atrial fibrillation detector 70 and the data acquisition means 48 are normally in a deactivated state and are activated only at predetermined spaced apart times. This greatly conserves power for extending the predicted lifetime of the defibrillator 30 because detection of atrial fibrillation is not continuously performed. When atrial fibrillation is not detected or when intervention for an atrial fibrillation episode is completed, the wakeup timer 90 is reset for once again activating atrial fibrillation detection at the next predetermined time.

While a particular embodiment of the present invention has been shown and described, modifications may be made, and it is therefore intended in the appended claims to cover all such changes and modifications which fall within the true spirit and scope of the invention.

What is claimed is:

1. An implantable atrial defibrillator for applying cardioverting electrical energy to the atria of a human heart in need of cardioversion, said atrial defibrillator comprising:

lead means for sensing electrical activity of the heart including the atria of the heart;

atrial fibrillation detecting means for detecting if the heart is in atrial fibrillation when said atrial fibrillation detecting means is activated, said atrial fibrillation detecting means having a normally deactivated state;

cardioverting means coupled to said lead means and being responsive to said atrial fibrillation detecting means detecting atrial fibrillation of the heart for applying cardioverting electrical energy to the atria of the heart to cardiovert the atria of the heart; and timing means for activating said atrial fibrillation detecting means at spaced apart predetermined times.

2. An implantable atrial defibrillator for applying cardioverting electrical energy to the atria of a human heart in need of cardioversion, said atrial defibrillator comprising:

lead means for sensing electrical activity of the heart including the atria of the heart;

atrial fibrillation detecting means for detecting if the heart is in atrial fibrillation when said atrial fibrillation detecting means is activated, said atrial fibrillation detecting means having a normally deactivated state;

cardioverting means coupled to said lead means and being responsive to said atrial fibrillation detecting means detecting atrial fibrillation of the heart for applying cardioverting electrical energy to the atria of the heart to cardiovert the atria of the heart;

activating means for activating said atrial fibrillation detecting means at spaced apart predetermined times; and data acquiring means coupled to said lead means for acquiring data associated with the sensed activity of the heart when said data acquiring means are activated, said data acquiring means including memory means for storing said acquired data, said atrial fibrillation detecting means including processing means for processing said stored data for detecting atrial fibrillation of the heart, said data acquiring means having a normally deactivated state, and said activating means activating said data acquiring means prior to activating said atrial fibrillation detecting means.

3. An implantable atrial defibrillator for applying cardioverting electrical energy to the atria of a human heart in need of cardioversion, said atrial defibrillator comprising;

lead means for sensing electrical activity of the heart including the atria of the heart;

atrial fibrillation detecting means for detecting if the heart is in atrial fibrillation when said atrial fibrillation detecting means is activated, said atrial fibrillation detecting means having a normally deactivated state;

cardioverting means coupled to said lead means and being responsive to said atrial fibrillation detecting means detecting atrial fibrillation of the heart for applying cardioverting electrical energy to the atria of the heart to cardiovert the atria of the heart: and activating means for activating said atrial fibrillation detecting means at spaced apart predetermined times, said activating means including timing means for timing a predetermined time interval.

4. An atrial defibrillator as defined in claim 3 wherein said timing means times said predetermined time interval responsive to said atrial fibrillation detecting means failing to detect atrial fibrillation.

5. An atrial defibrillator as defined in claim 3 wherein said timing means times said predetermined time interval responsive to said cardioverting means cardioverting the atria of the heart.

* * * * *